US006365399B1

(12) United States Patent
Takashima et al.

(10) Patent No.: US 6,365,399 B1
(45) Date of Patent: Apr. 2, 2002

(54) **PROCESS FOR PRODUCING CARBOXYLIC ACID ISOMER USING *NOCARDIA DIAPHANOZONARIA* OR *SACCHAROPOLYSPORA HIRSUTA***

(75) Inventors: Yoshiki Takashima, Nishinomiya; Yuko Kobayashi, Toyonaka, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/625,323

(22) Filed: Jul. 25, 2000

(30) Foreign Application Priority Data

Aug. 9, 1999 (JP) .......................................... 11-225210

(51) Int. Cl.$^7$ ................................................ C12P 41/00
(52) U.S. Cl. ........................................................ 435/280
(58) Field of Search ......................................... 435/280

(56) References Cited

U.S. PATENT DOCUMENTS

| 4,565,782 A | 1/1986 | Bewick ...................... 435/122 |
| 4,568,641 A | 2/1986 | Bewick ...................... 435/122 |
| 5,043,274 A | 8/1991 | Reid et al. .................. 435/135 |
| 5,108,917 A | 4/1992 | Bertola et al. .............. 435/136 |
| 5,283,193 A | 2/1994 | Yamamoto et al. ......... 435/280 |

FOREIGN PATENT DOCUMENTS

GB    2 218 985    11/1999

OTHER PUBLICATIONS

Hung et al., "Chiral inversion of 2–phenylpropionic Acid by *Coryceps militaris*", J. Appl. Bacteriology 81 : 242–50 (1996).*
ATCC Catalogue Bacteria and Bacteriophages, p. 314, (1996).*
M.J. Thomason et al., "The stereo inversion of 2–arylpropionic acid non–sterioidal anti–inflammatory drugs and structurally related compounds by *Verticillium lecanii*", Journal of Applied Microbiology, vol. 85, 1998, pp. 155–163.

\* cited by examiner

*Primary Examiner*—Sandra E. Saucier
(74) *Attorney, Agent, or Firm*—Sughrue Mion, PLLC

(57) ABSTRACT

The present invention provides a process for producing a carboxylic acid isomer B represented by the general formula (2):

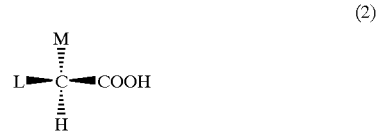

(2)

(wherein, L is a $C_6$ to $C_{14}$ aryl group which may optionally been substituted, $C_4$ to $C_{12}$ heteroaryl group which may optionally been substituted, $C_6$ to $C_{14}$ aryloxy group which may optionally been substituted or $C_4$ to $C_{12}$ heteroaryloxy group which may optionally been substituted, and M is an $C_1$ to $C_3$ alkyl group.), which comprises:

allowing a carboxylic acid isomer A represented by the general formula (1):

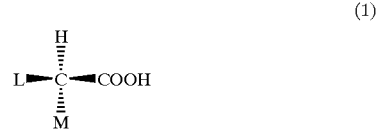

(1)

(wherein, L and M have meanings as defined above.) to contact with a microbiological material having an ability to convert the carboxylic acid isomer A(1) into the carboxylic acid isomer B(2), and the like. According to the present invention, the carboxylic acid isomer B(2) useful as an intermediate of medicines, agricultural chemicals and like can be produced efficiently.

8 Claims, No Drawings

PROCESS FOR PRODUCING CARBOXYLIC ACID ISOMER USING *NOCARDIA DIAPHANOZONARIA* OR *SACCHAROPOLYSPORA HIRSUTA*

BACKGROUND OF THE INVENTION

1. Field of the Invention

The present invention relates to a process for producing a carboxylic acid isomer.

2. Description of the Related Art

Carboxylic acids are widely used as intermediates of medicines such as an anti-inflammatory agent and the like and intermediates of agricultural chemicals such as a herbicide and the like, and optical isomers corresponding to the configurations of intended medicines and agricultural chemicals are required.

A method for producing a compound using a microorganism, so called bioconversion method can be generally conducted under mild condition, and is effective in small waste load, and the like and recognized as an advantageous method. There is known a method in which a certain microorganism is allowed to act on a compound (X) represented by the general formula (X):

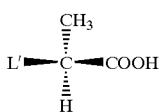

(X)

(wherein, L' is an aryl group or aryloxy group.) to produce a compound (Y) represented by the general formula (Y):

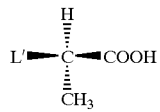

(Y)

(wherein, L' has the same meaning as defined above.), according to a bioconversion method (Japanese Patent Application Laid-Open (JP-A) No. 2-65785, J. Appl. Microbiol., 85, 155–163 (1998), JP-A Nos. 60-43388, 60-43389, and the like.). However, the compound obtained by this method is limited to the compound (Y), and a method for producing the reverse optical isomer efficiently has been required.

SUMMARY OF THE INVENTION

Under such conditions, the present inventors have intensively studied, a process for producing a carboxylic acid isomer, and resultantly found a microorganism having an ability to produce a carboxylic acid isomer B represented by the general formula (2):

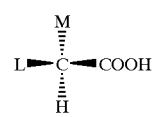

(2)

(wherein, L is a $C_6$ to $C_{14}$ aryl group which may optionally been substituted, $C_4$ to $C_{12}$ heteroaryl group which may optionally been substituted, $C_6$ to $C_{14}$ aryloxy group which may optionally been substituted or $C_4$ to $C_{12}$ heteroaryloxy group which may optionally been substituted, and M is an $C_1$ to $C_3$ alkyl group.), (hereinafter, referred to as the carboxylic acid isomer B(2)) by reversing the configuration based on an asymmetric carbon atom of a carboxylic acid, and further found that the carboxylic acid isomer B(2) can be obtained in high yield by using this microorganism, leading to completion of the present invention.

Namely, the present invention provide:

1. A process for producing a carboxylic acid isomer B represented by the general formula (2):

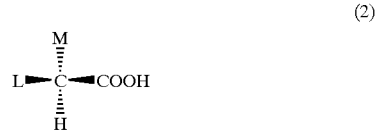

(2)

(wherein, L is a $C_6$ to $C_{14}$ aryl group which may optionally been substituted, $C_4$ to $C_{12}$ heteroaryl group which may optionally been substituted, $C_6$ to $C_{14}$ aryloxy group which may optionally been substituted or $C_4$ to $C_{12}$ heteroaryloxy group which may optionally been substituted, and M is an $C_1$ to $C_3$ alkyl group.), which comprises:

allowing a carboxylic acid isomer A represented by the general formula (1):

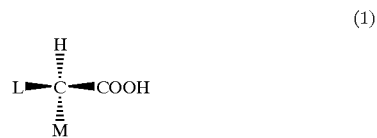

(1)

(wherein, L and M have meanings as defined above.) to contact with a microbiological material having an ability to convert the carboxylic acid isomer A(1) into the carboxylic acid isomer B(2).

2. The process according to the above 1, wherein L in the carboxylic acid isomer A(1) is a $C_6$ to $C_{14}$ aryl group which may optionally been substituted or $C_4$ to $C_{12}$ heteroaryl group which may optionally been substituted.

3. The process according to the above 1, wherein M in the carboxylic acid isomer A(1) is a methyl group.

4. The process according to the above 1, wherein the microbiological material is a cultured broth of microbial cells, microbial cells or materials obtainable by treating a microorganism belonging to Actinomycetes group.

5. The process according to the above 1 wherein the microbiological material is a cultured broth of microbial cells, microbial cells or materials obtainable by treating a microorganism belonging to the genus Nocardia.

6. The process according to the above 1, wherein the microbiological material is a cultured broth of microbial cells, microbial cells or materials obtainable by treating a microorganism of Nocardia diaphanozonaria JCM3208 or a mutant thereof.

7. The process according to the above 1 wherein the microbiological material is a cultured broth of microbial cells, microbial cells or materials obtainable by treating a microorganism belonging to the genus Saccharopolyspora.

8. The process according to the above 1, wherein the microbiological material is a cultured broth of microbial cells, microbial cells or materials obtainable by treating a microorganism of Saccharopolyspora hirsuta subsp. Kobensis JCM 9109 or a mutant thereof.

9. A process for improving the optical purity of a carboxylic acid isomer B represented by the general formula (2):

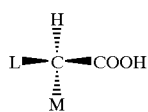
(1)

(wherein, L is a $C_6$ to $C_{14}$ aryl group which may optionally been substituted, $C_4$ to $C_{12}$ heteroaryl group which may optionally been substituted, $C_6$ to $C_{14}$ aryloxy group which may optionally been substituted or $C_4$ to $C_{12}$ heteroaryloxy group which may optionally been substituted, and M is an $C_1$ to $C_3$ alkyl group.), which comprises:
allowing a carboxylic acid by the general formula (3):

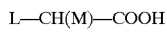

(wherein, L and M have meanings as defined above.) to contact with a microbiological material having an ability to convert a carboxylic acid isomer A represented by the general formula (1):

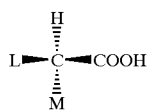
(1)

(wherein, L and M have meanings as defined above.) into the carboxylic acid isomer B(2).

10. A use of a microbiological material having an ability to convert a carboxylic acid isomer A represented by the general formula (1):

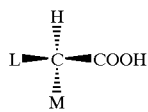
(1)

(wherein, L is a $C_6$ to $C_{14}$ aryl group which may optionally been substituted, $C_4$ to $C_{12}$ heteroaryl group which may optionally been substituted, $C_6$ to $C_{14}$ aryloxy group which may optionally been substituted or $C_4$ to $C_{12}$ heteroaryloxy group which may optionally been substituted, and M is an $C_1$ to $C_3$ alkyl group.)
into a carboxylic acid isomer B represented by the general formula (2):

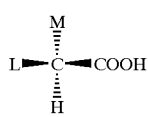
(2)

(wherein, L and M have meanings as defined above.). for converting the carboxylic acid isomer A(1) into the carboxylic acid isomer B(2).

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

DETAILED DESCRIPTION OF THE PREFERRED EMBODIMENTS

In the process of the present invention, L in the carboxylic acid isomer A(1) is a $C_6$ to $C_{14}$ aryl group which may optionally been substituted (i.e. $C_6$ to $C_{14}$ aryl group or substituted $C_6$ to $C_{14}$ aryl group), $C_4$ to $C_{12}$ heteroaryl group which may optionally been substituted (i.e. $C_4$ to $C_{12}$ heteroaryl group or substituted $C_4$ to $C_{12}$ heteroaryl group), $C_6$ to $C_{14}$ aryloxy group which may optionally been substituted (i.e. $C_6$ to $C_{14}$ aryloxy group or substituted $C_6$ to $C_{14}$ aryloxy group) or $C_4$ to $C_{12}$ heteroaryloxy group which may optionally been substituted (i.e. $C_4$ to $C_{12}$ heteroaryloxy group or substituted $C_4$ to $C_{12}$ heteroaryloxy group). Examples of the $C_6$ to $C_{14}$ aryl group include a phenyl group, naphthyl group and the like. Preferable examples of the $C_4$ to $C_{12}$ heteroaryl group include those containing, as a hetero atom, 1 to 4 of at least one kind of atom among nitrogen, oxygen and sulfur atoms, and there specifically are listed

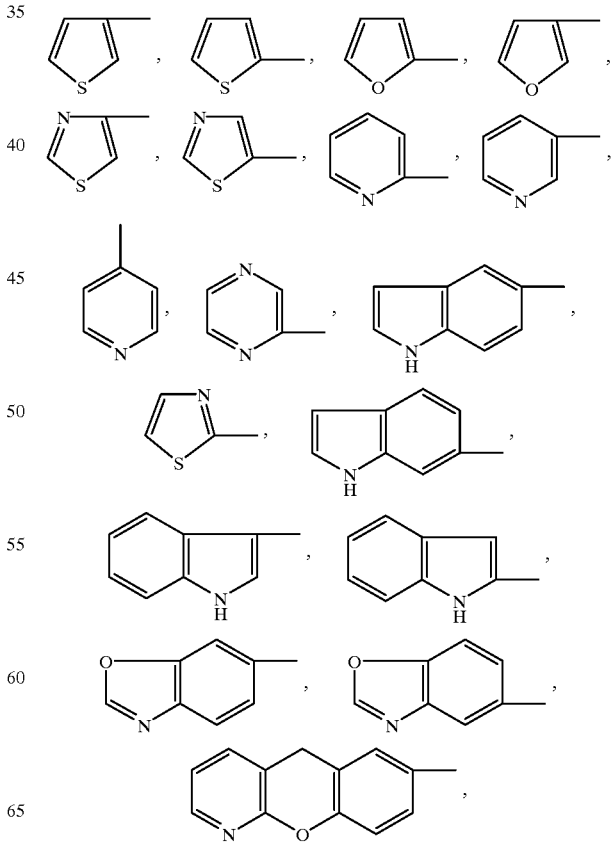

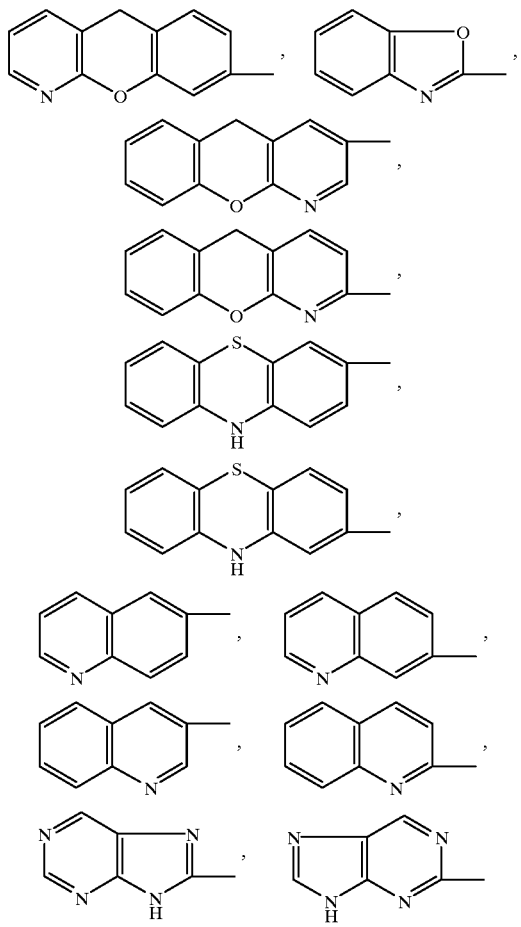

and the like.

Examples of the $C_6$ to $C_{14}$ aryloxy group include a phenyloxy group, naphthyloxy group and the like. Preferable examples of the $C_4$ to $C_{12}$ heteroaryloxy group include those containing, as a hetero atom, 1 to 4 of at least one kind of atom among nitrogen, oxygen and sulfur atoms in addition to an oxy group connected to a heteroaryl group, and there specifically are listed

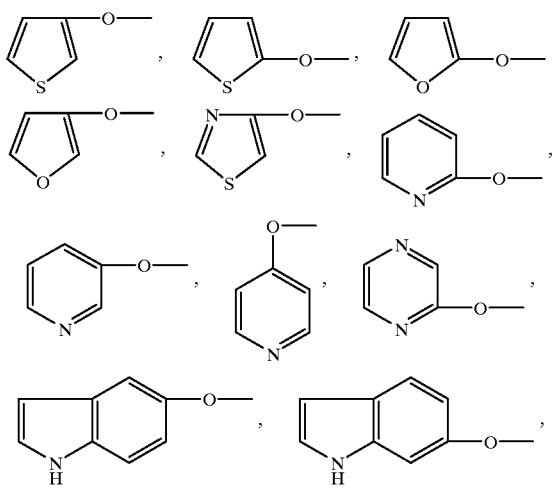

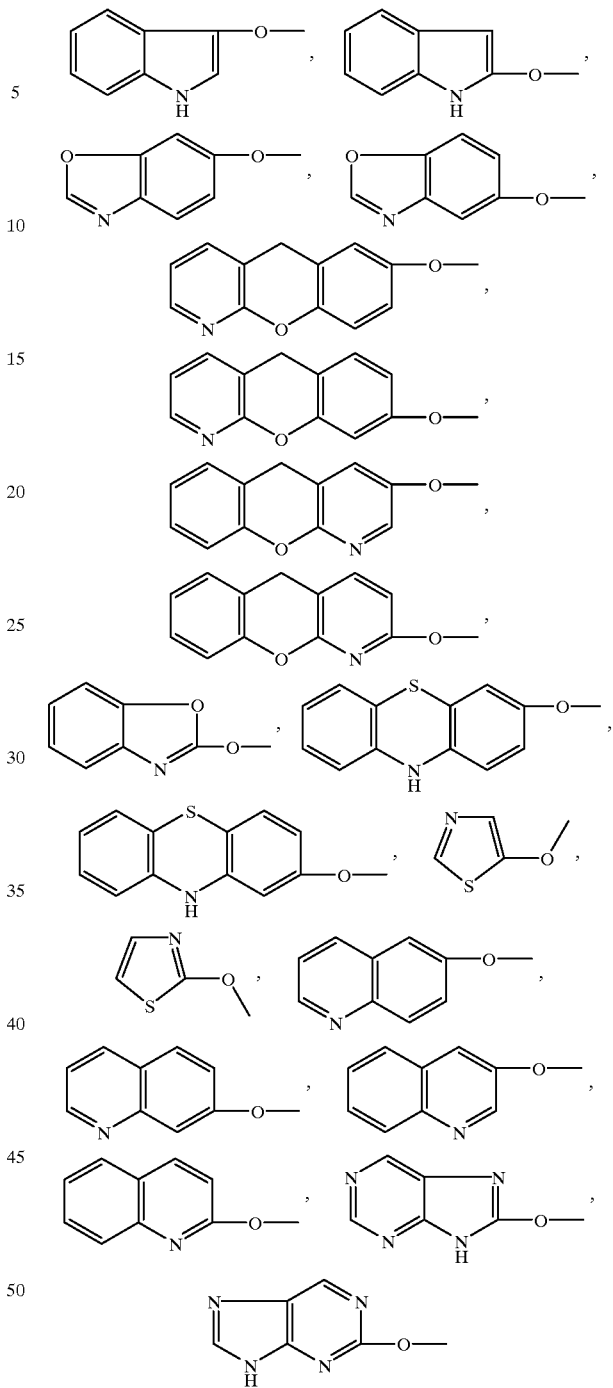

and the like.

Examples of the substituent on the substituted $C_6$ to $C_{14}$ aryl group, the substituted $C_4$ to $C_{12}$ heteroaryl group, the substituted $C_6$ to $C_{14}$ aryloxy group or the substituted $C_4$ to $C_{12}$ heteroaryloxy group represented by L include a phenyl group; phenyl groups substituted by one or more of $C_1$ to $C_3$ alkyl groups, $C_1$ to $C_3$ alkoxy groups, amino group, cyano group, hydroxyl group and halogen atoms; a phenoxy group; phenoxy groups substituted by one or more of $C_1$ to $C_3$ alkyl groups, $C_1$ to $C_3$ alkoxy groups, amino group, cyano group, hydroxyl group and halogen atoms; a benzoyl group; benzoyl groups substituted by one or more of $C_1$ to $C_3$ alkyl groups, $C_1$ to $C_3$ alkoxy groups, amino group, cyano group, hydroxyl group and halogen atoms; a thenoyl group; a pyrrolyl group which may be condensed with a benzene ring; pyridinoimidazolyl group; oxazolyl group which may be condensed with a benzene ring; a pyrrolidin-2-on-1-yl group which may be condensed with a benzene ring; a benzyloxy group; a pyridyl group; pyridyl groups substituted by one or more of $C_1$ to $C_3$ alkyl groups, $C_1$ to $C_3$ haloalkyl groups, $C_1$ to $C_3$ alkoxy groups and halogen atoms; a pyridyloxy group; pyridyloxy groups substituted by one or more of $C_1$ to $C_3$ alkyl groups, $C_1$ to $C_3$ haloalkyl groups, $C_1$ to $C_3$ alkoxy groups and halogen atoms; $C_1$ to $C_6$ alkyl groups; $C_1$ to $C_6$ alkyl groups substituted by one or more of $C_1$ to $C_3$ alkoxy groups, amino group, cyano group, hydroxyl group and halogen atoms; $C_1$ to $C_3$ alkoxy groups; $C_1$ to $C_3$ alkylthio groups; methylenedioxy group; hydroxyl group; cyano group; carboxyl group; $C_2$ to $C_5$ alkyloxycarbonyl groups; amino group; mono or di($C_1$ to $C_5$) alkylamino groups; mono or di($C_3$ to $C_5$) alkenylamino groups; an aminocarbonyl group; and halogen atoms. One or more, usually from 1 to 5 of hydrogen atoms on the $C_6$ to $C_{14}$ aryl group, $C_4$ to $C_{12}$ heteroaryl group, $C_6$ to $C_{14}$ aryloxy group or $C_4$ to $C_{12}$ heteroaryloxy represented by L are substituted by the same or different substituents described above.

Preferable examples of the above-mentioned substituent include a phenyl group, p-chlorophenyl group, p-hydroxyphenyl group, phenoxy group, p-chlorophenoxy group, p-hydroxyphenoxy group, benzoyl group,

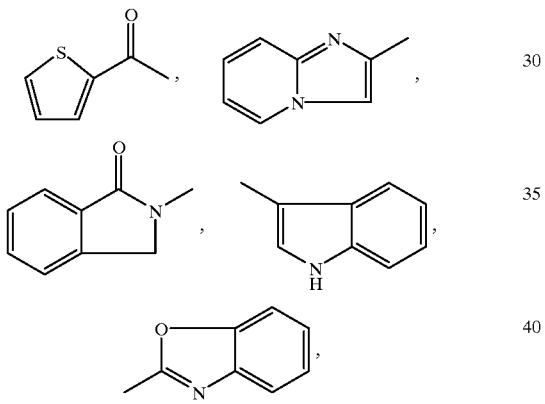

benzyloxy group, 2-pyridyl group, 3-pyridyl group, 4-pyridyl group, 2-pyridyloxy group, 3-pyridyloxy group, 4-pyridyloxy group, 5-trifluoromethyl-2-pyridyloxy group, 3-chloro-5-trifluoromethyl-2-pyridyloxy group, 2,3-methylenedioxydiphenyl group, 3,4-methylenedioxydiphenyl group, methyl group, ethyl group, butyl group, isobutyl group, monochloromethyl group, trifluoromethyl group, methoxy group, ethoxy group, methylthio group, ethylthio group, aminocarbonyl group, methylenedioxy group, hydroxyl group, cyano group, amino group, carboxyl group, methoxycarbonyl group, ethoxycarbonyl group, fluorine atom, chlorine atom and bromine atom.

Examples of L include a phenyl group, 3,5-dichlorophenyl group, 2,4-dichlorophenyl group, 4-chloro-2-nitrophenyl group, 4-isobutylphenyl group, 3-benzoylphenyl group, 3-fluoro-4-phenylphenyl group, 3-phenoxyphenyl group, p-chlorophenoxyphenyl group, 1-naphthyl group, 2-naphthyl group, 6-methoxy-2-naphthyl group, 4-chloro-2-methylphenyl group, 4-hydroxyphenyl group, 4-isobutenylaminophenyl group, 4-(5-trifluoromethylpyridyl-2-oxy)phenyl group, 4-(3-chloro-5-trifluoromethylpyridyl-2-oxy)-phenyl group, 2-pyridyl group, 3-pyridyl group, 4-pyridyl group, phenoxy group, 3,5-dichlorophenoxy group, 2,4-dichlorophenoxy group, 4-chloro-2-nitrophenoxy group, 4-isobutylphenoxy group, 3-benzoylphenoxy group, 3-fluoro-4-phenylphenoxy group, 3-phenoxyphenoxy group, p-chlorophenoxyphenoxy group, 1-naphthyloxy group, 2-naphthyloxy group, 6-methoxy-2-naphthyloxy group, 4-chloro-2-methylphenyloxy group, 4-isobutenylaminophenoxy group, 4-(5-trifluoromethylpyridyl-2-oxy)phenoxy group, 4-(3-chloro-5-trifluoromethylpyridyl-2-oxy)-phenoxy group, 2-pyridyloxy group, 3-pyridyloxy group, 4-pyridyloxy group,

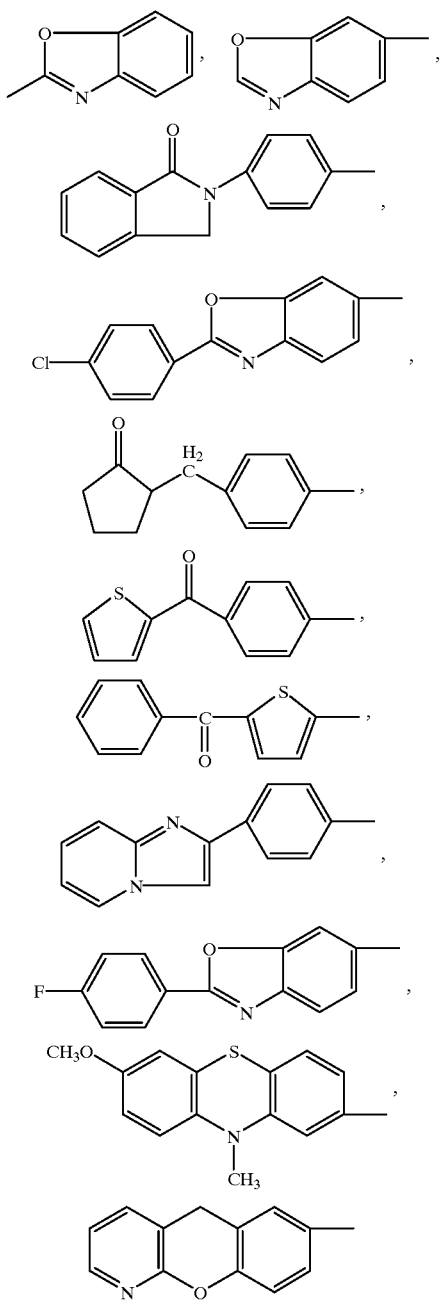

and the like.

Examples of the $C_1$ to $C_3$ alkyl group represented by M in the carboxylic acid isomer A(1) in the process of the present invention include a methyl group, ethyl group, n-propyl group and isopropyl group.

Specific examples of the carboxylic acid isomer A(1) include
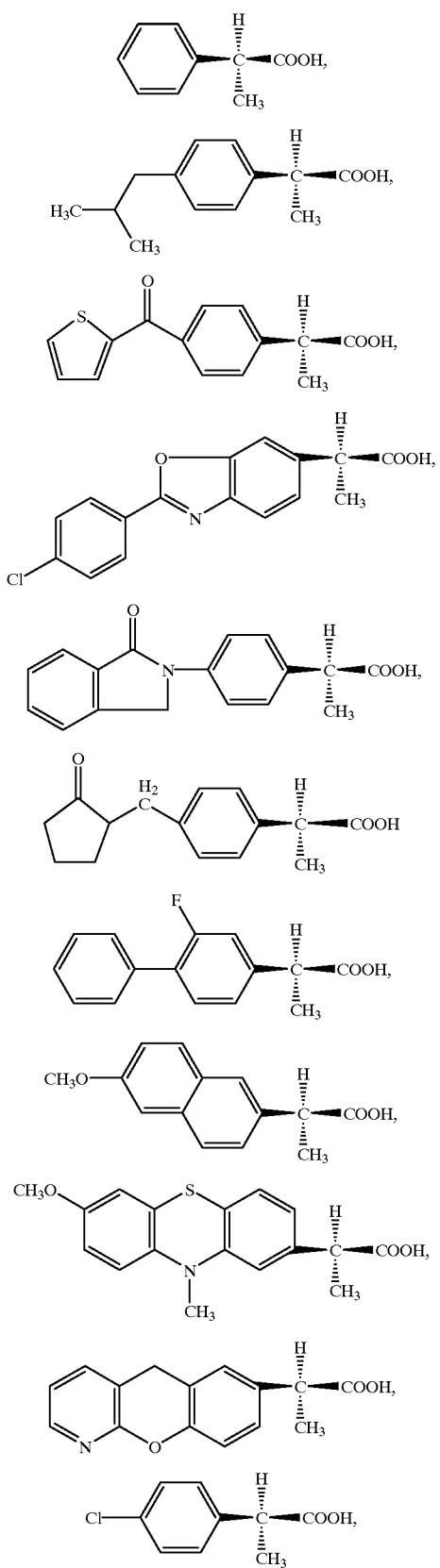
-continued
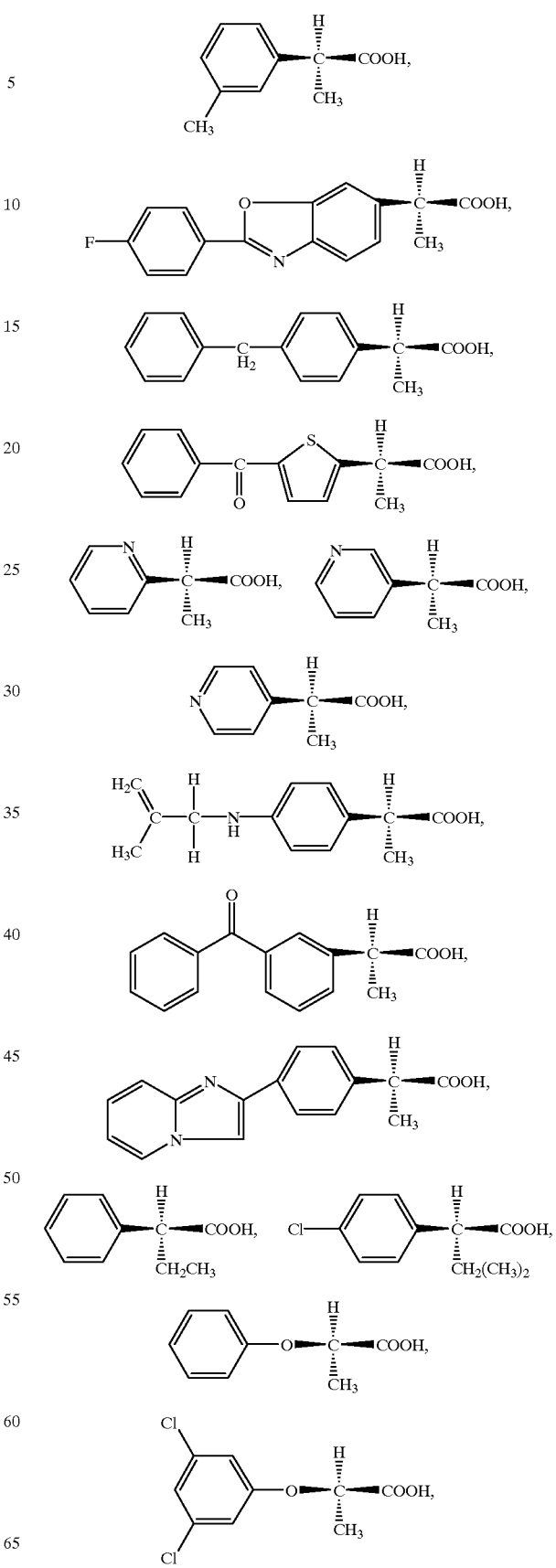

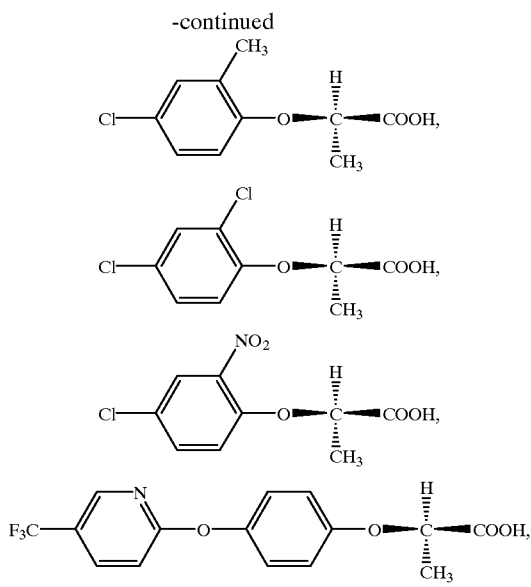

and the like.

Examples of the raw material in the production process of the present invention include the carboxylic acid isomers A(1), mixtures of the carboxylic acid isomers A(1) and the carboxylic acid isomers B(2), and the like. Also when a mixture of the carboxylic acid isomer A(1) and the carboxylic acid isomer B(2) is used, the carboxylic acid isomer A(1) selectively reacts to be converted into the carboxylic acid isomer B(2). The mixing ratio of the carboxylic acid isomer A(1) to the carboxylic acid isomer B(2) is not particularly restricted, and use of a racemate (1:1 mixture of the carboxylic acid isomer A(1) to the carboxylic acid isomer B(2)) is advantageous from the industrial standpoints such as the cost of raw materials, availability and the like.

The process of the present invention is usually conducted in water, or in a buffer containing an inorganic acid salt such as an alkali metal phosphate and the like such as sodium phosphate, potassium phosphate and the like, an organic acid salt such as an alkali metal acetate and the like such as sodium acetate, potassium acetate and the like, and the concentration of the raw material in the reaction solution may be about 30% (w/v) or less, and preferably about 0.01 to 20% (w/v). The use amount of the microbiological material of the present invention is appropriately determined, for example, in view of the reaction time and the extent of the reactivity per the microbiological material. For example, it may be from 0.01 to 200-fold by weight, preferably from 0.1 to 50-fold by weight based on the raw material. The reaction temperature may be from about 10 to 70° C., and preferably from about 20 to 60° C. The pH value of the reaction solution may be from 4 to 12, and preferably from about 5 to 11. The reaction time may be set depending on, for example, the production ratio of the desired carboxylic acid isomer B(2), and the like. Usually, it may be from about 16 to 240 hours, and it may also be determined by appropriately tracing the termination of the reaction by analysis of sampling using liquid chromatography and the like.

Further, the addition of a surfactant, coenzyme, metal salt, micronutrient, organic solvent and the like as an auxiliary agent to the reaction solution may sometimes be effective for the reduction of the reaction time and the improvement of the conversion ratio, and if necessary, these auxiliary agents may also be added to the reaction solution alone or in combination. Specific examples of the surfactant include sodium dodecylsulfate, polyethylene glycol mono-p-isooctyl phenyl ether, cetylpyridium bromide and the like. Specific examples the coenzyme include nicotineamide adenine nucleotide, pyridoxal phosphate, coenzyme A and the like. Specific examples of the metal salt include potassium dihydrogen phosphate, disodium hydrogen phosphate, magnesium sulfate penta-hydrate, ferrous sulfate penta-hydrate, zinc sulfate penta-hydrate, manganese sulfate tri-hydrate, cobalt chloride hexa-hydrate and the like. Specific examples of the micronutrient include yeast extract and the like. Specific examples of the organic solvent include alkanes such as n-heptane, cyclohexane, isooctane and the like; ethers such as methyl-tert-butyl ether and the like; alcohols such as methanol, isopropanol, n-octanol and the like; sulfoxides such as DMSO and the like; ketones such as acetone and the like; keto acids such as oxaloacetic acid, pyruvic acid, α-ketobutyric acid and the like; alkyl esters of keto acids such as methyl pyruvate and the like.

Thus obtained carboxylic acid isomer B(2) may be recovered from the reaction solution by appropriately combining known methods. For example, the microbiological material of the present invention is separated by centrifugal separation and the like from the reaction solution, then, the supernatant is controlled to acidic, extracted and separated with an organic solvent such as toluene, heptane, diethyl ether and the like to remove an aqueous phase, then, the organic solvent is distilled under reduced pressure to obtain the carboxylic acid isomer B(2). Further, the carboxylic acid isomer B(2) may be purified by column chromatography and the like, if necessary.

The microbiological material used in the present invention (hereinafter, referred to as the microbiological material of the present invention) means a cultured broth of microbial cells, microbial cells or materials obtainable by treating a microorganism having an ability to convert the carboxylic acid isomer A(1) into the carboxylic acid isomer B(2).

The microorganism used in the present invention may be a wild strain of a microorganism separated from natural field, or may be a variant (i.e. mutant) derived from the wild strain by a chemical mutagen, ultraviolet ray and the like, provided that it has the above-described ability. The microorganism may be selected based on, for example, the ability to convert the carboxylic acid isomer A(1), for example, (S)-2-phenylpropioninc acid into the carboxylic acid isomer B(2), for example, (R)-2-phenylpropionic acid. More specific explanation will be described in the following Example 1.

Specific example of the microorganism used in the present invention, microorganisms belonging to Actinomycetes group, for example, the genus Nocardia and the genus Saccharopolyspora. Preferable example include Nocardia diaphanozonaria and Saccharopolyspora hirsuta, and specific example thereof include Nocardia diphanozonaria JCM3208 and Saccharopolyspora hirsuta subsp. Kobensis JCM 9109.

For culturing of the microorganism used in the present invention, various culturing mediums containing carbon sources, nitrogen sources, organic or inorganic salt s and the like used in usual culturing of microorganisms may be used. Examples of the carbon source include saccharides such as glucose, fructose, sucrose, dextrin and the like, sugar alcohols such as glycerol, sorbitol and the like, organic acids such as fumaric acid, citric acid, pyruvic acid and the like. The addition amount of the carbon sources to a culturing medium may be from about 0.1 to 10% (w/v). Examples of the nitrogen source include ammonium salts of inorganic acids such as ammonium chloride, ammonium sulfate, ammonium phosphate and the like, ammonium salts or organic acids such as ammonium fumarate, ammonium citrate and the like, natural organic nitrogen sources such as meat extract, yeast extract, wheat germ extract, soy bean powder, corn steep liquor, cotton seed powder, dry yeast, casein hydrolyzate and the like, or amino acids. Among them, the natural organic nitrogen source or amino acids may be used together as the carbon source in many case. The addition amount of the nitrogen source may be from about 0.1 to 10% (w/v). Examples of the inorganic salts include phosphate salts such as mono-potassium phosphate, dipotassium phosphate, mono-sodium phosphate, di-sodium phosphate and the like; chloride salts such as potassium chloride, sodium chloride, cobalt chloride hexa-hydrate and the like; sulfate salts such as magnesium sulfate, ferrous sulfate hepta-hydrate, zinc sulfate hepta-hydrate, manganese sulfate tri- hydrate and the like. The addition amount of the inorganic salts may be from about 0.0001% (w/v) to 1% (w/v).

Culturing of the microorganism used in the present invention may be conducted according to conventional methods in the field of microbiology, and any of solid culturing and liquid culturing (test tube shaking-type culturing, reciprocating-type shaking culturing, Jar Fermenter culturing, Tank Fermentation and the like) may be used. When Jar Fermenter is used in liquid culturing, it is necessary to introduce sterile air into Jar Fermenter, and it is usually conducted under ventilation condition about 0.1 to about 2-fold/min. based on the liquid-amount of the culturing medium.

The culturing temperature may be changed in the range wherein a microorganism grows, and for example from about 15° C. to about 40° C., and the culturing pH may be for example from about 6 to about 8, preferably. The culturing time may be for example from about 1 day to about 10 days, though it varies depending on the culturing condition.

The microbiological material of the present invention includes various forms such as, for example, a cultured broth of microbial cells, microbial cells or materials obtainable by treating a microorganism used in the present invention. Herein, materials obtainable by treating a microorganism means, for example, freeze-dried microbial cells, acetone dried microbial cells, microbial cell ground material, autolyzed microbial cells, microbial cell ultrasonic-treated material, microbial cell extract, enzyme, microbial cell alkali-treated material and the like, or that obtained by insolubilizing those treated materials, a cultured broth of microbial cells and microbial cells and the like according to for example a carrier bonding method in which they are bonded or adsorbed onto an inorganic carrier such as silica gel, ceramics and the like, cellulose, ion exchange resin and the like, or an enclosure method in which they are enclosed in polymer network structure such as polyacrylamide, sulfur-containing polysaccharide gel (for example, carageenan), alginic acid gel, agar gel and the like, and by processing the product into easily-separable condition (solidified material).

EXAMPLE

The present invention will be explained more specifically by the following examples, but the examples do not limit the scope of the present invention.

The quantitative analysis and optical isomer analysis of 2-phenylpropionic acid and 2-phenoxypropionic acid were carried out by gas chromatography under the following conditions.

Column: Chirasil-DEX'CB (manufactured by Chrom Pac, length: 25 m, internal diameter: 0.32 mm)
Column temperature: 150° C.
Detector: Flame ion method Example 1
(Screening of Microorganism)

One gram of Soil collected from the nature is added to 5 ml of sterilized water, and then the mixture is suspended. After the mixture is left for 5 minutes to separate a supernatant form the mixture, 0.1 ml of the supernatant is spread and cultured at 30° C. on a agar containing a culturing medium composed of 0.5 wt % of peptone, 0.3 wt % of meat extract and 0 to 0.5 wt % of various carboxylic acids represented by the general formula (3) or the carboxylic acid isomers A(1) to allow formation of a colony. Then, microorganisms having an ability to convert the carboxylic acid isomer A(1) into the carboxylic acid isomer B(2) are selected from colony-forming microorganisms.

The selection of the microorganisms are conducted as described below. The microorganisms forming a colony are cultured in a test tube at 30° C. for three days while shaking in a sterile medium (pH 7.0) comprising 1.0% (w/v) of glycerol, 0.2% (w/v) of polypeptone (manufactured by Nippon Seiyaku Corp.), 0.3% (w/v) of meat extract powder (manufactured by Kyokuto Seiyaku Corp.), 0.3% (w/v) of yeast extract (manufactured by Difco), 0.1% (w/v) of di-potassium phosphate, 0.1% (w/v) of mono-potassium phosphate and 0.03% (w/v) of magnesium sulfate heptahydrate.

Microbial cells are collected from this cultured broth by centrifugal separation (10000×g, 10 minutes), and to this is added 10 ml of 100 mM potassium phosphate buffer (pH 7.0) to form a suspension again, and microbial cells are collected by centrifugal separation (10000×g, 10 minutes) to obtain wet microbial cells. Thus obtained microbial cells are suspended in 1 ml of 100 mM potassium phosphate buffer (pH 7.0) to obtain a microbial cell suspension. The resulting microbial cell suspension (0.3 ml) and 2.7 ml of 5.55 mM (S)-2-phenylpropionic acid/100 mM potassium phosphate buffer (pH 7.0) are charged into a test tube, and this is incubated at 30° C. while being shaken in reciprocation (250 times/min., amplitude 2 cm). After 190 hours, a part of the reaction solution is collected, the microbial cell is removed by centrifugal separation and the resulted supernatant is collected, then, the quantitative analysis and optical isomer analysis of 2-phenylpropionic acid are conducted by gas chromatography. The intended microorganism can be obtained by specifying microorganisms having an optical isomer R/S ratio, which is more than 1, of 2-phenylpropionic acid based on the result of the analysis.

Example 2

Into a 500 mL Sakaguchi flask charged with 100 ml of a culturing medium (pH 7.0) comprising 1.0% (w/v) of glycerol, 0.2% (w/v) of polypeptone (manufactured by Nippon Seiyaku Corp.), 0.3% (w/v) of meat extract powder (manufactured by Kyokuto Seiyaku Corp.), 0.3% (w/v) of yeast extract (manufactured by Difco), 0.1% (w/v) of di-potassium phosphate, 0.1% (w/v) of mono-potassium phosphate and 0.03% (w/v) of magnesium sulfate heptahydrate was inoculated with 1 mL of a culturing medium of Nocardia diphanozonaria JCM3208 cultured previously in a culturing medium having the same composition, and cultured at 30° C. for 3 days while being shaken in reciprocation.

Microbial cells are collected from the obtained cultured broth by centrifugal separation (10000×g, 10 min.), and to this is added 10 ml of a 100 mM potassium phosphate buffer (pH 7.0) to form a suspension again, and microbial cells are collected by centrifugal separation (10000×g, 10 minutes) to obtain microbial cells. Thus obtained wet microbial cells are suspended in 10 ml of 100 mM potassium phosphate pH 7.0) to obtain a microbial cell suspension. (S)-2-phenylpropionic acid is dissolved into 100 mM potassium phosphate buffer (pH 7.0) to obtain a concentration of 5.55 mM which is used as substrate solution. To 2.7 ml of the substrate solution is added 0.3 ml of the microbial cell suspension in a test tube, and incubated at 30° C. while being shaken in reciprocation (250 times/min., amplitude 2 cm). After 190 hours, a part of the reaction solution is collected, the microbial cell is removed by centrifugal separation and the resulted supernatant is collected, then, analyzed by gas chromatography. As a result, 4.3 mM of 2-phenylpropionic acid in the reaction solution having an optical isomer R:S ratio of 80:20 was detected.

On the other hand, the same operation was conducted in the above-described example except that (R)-2-phenylpropionic acid was used instead of (S)-2-phenylpropionic acid. After 190 hours, a part of the reaction solution was collected, the microbial cell was removed by centrifugal separation and the resulted supernatant was collected, then, analyzed by gas chromatography. As a result, no (S)-2-phenylpropionic acid was detected.

Example 3

(Racemic)-2-phenylpropionic acid was dissolved into 100 mM potassium phosphate buffer (pH 7.0) to obtain a concentration of 7.4 mM. To thus obtained substrate solution (2.7 ml) was added 0.3 ml of microbial cell suspension prepared in the same manner as in Example 2, and incubated at 30° C. while being shaken in reciprocation (250 times/min., amplitude 2 cm). After 72 hours, a part of the reaction solution was collected, the microbial cell was removed by centrifugal separation and the resulted supernatant was collected, then, analyzed by gas chromatography. As a result, 6.5 mM of 2-phenylpropionic acid in the reaction solution having an optical isomer R:S ratio of 60:40 was detected.

Example 4

Into a 500 mL Sakaguchi flask charged with 100 ml of a culturing medium (pH 7.0) comprising 1.0% (w/v) of glycerol, 0.2% (w/v) of polypeptone (manufactured by Nippon Seiyaku Corp.), 0.3% (w/v) of meat extract powder (manufactured by Kyokuto Seiyaku Corp.), 0.3% (w/v) of yeast extract (manufactured by Difco), 0.1% (w/v) of di-potassium phosphate, 0.1% (w/v) of mono-potassium phosphate and 0.03% (w/v) of magnesium sulfate heptahydrate was inoculated with 1 mL of a culturing medium of Saccharopolyspora hirsuta subsp. Kobensis JCM 9109 cultured previously in a culturing medium having the same composition, and cultured at 30° C. for 3 days while being shaken in reciprocation.

Microbial cells are collected from the obtained cultured broth by centrifugal separation (10000×g, 10 min.), and to this is added 10 ml of a 100 mM potassium phosphate buffer (pH 7.0) to form a suspension again, and microbial cells are collected by centrifugal separation (10000×g, 10 minutes) to obtain microbial cells. Thus obtained wet microbial cells are suspended in 10 ml of 100 mM potassium phosphate (pH 7.0) to obtain a microbial cell suspension. (racemic)-2-phenoxypropionic acid is dissolved into 100 mM potassium phosphate buffer (pH 7.0) to obtain a concentration of 5.55 mM which is used as substrate solution. To 2.7 ml of the substrate solution is added 0.3 ml of the microbial cell suspension in a test tube, and incubated at 30° C. while being shaken in reciprocation (250 times/min., amplitude 2 cm). After 190 hours, a part of the reaction solution is collected, the microbial cell is removed by centrifugal separation and the resulted supernatant is collected, then, analyzed by gas chromatography. As a result, 5.1 mM of 2-phenoxypropionic acid in the reaction solution having an optical isomer R:S ratio of 70:30 was detected.

Example 5

(Racemic)-2-phenoxypropionic acid was dissolved into 100 mM potassium phosphate buffer (pH 7.0) to obtain a concentration of 5.55 mM. To thus obtained substrate solution (2.7 ml) was added 0.3 ml of microbial cell suspension prepared in the same manner as in Example 2, and incubated at 30° C. while being shaken in reciprocation (250 times/min., amplitude 2 cm). After 118 hours, a part of the reaction solution was collected, the microbial cell was removed by centrifugal separation (10000 g, 10 minutes) and the resulted supernatant was collected, then, analyzed by gas chromatography. As a result, 5.0 mM of 2-phenoxypropionic acid in the reaction solution having an optical isomer R:S ratio of 97:3 was detected.

According to the present invention, the carboxylic acid isomer B(2) useful as an intermediate of medicines, agricultural chemicals and like can be produced efficiently.

What is claimed is:

1. A process for producing a carboxylic acid isomer B represented by the general formula (2):

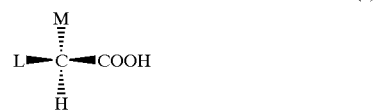

(2)

wherein L is a $C_6$ to $C_{14}$ aryl group which may optionally be substituted, a $C_4$ to $C_{12}$ heteroaryl group which may optionally be substituted, a $C_6$ to $C_{14}$ aryloxyl group which may optionally be substituted or a $C_4$ to $C_{12}$ heteroaryloxy group which may optionally be substituted, and M is a $C_1$ to $C_3$ alkyl group, which comprises:

allowing a carboxylic acid isomer A represented by the general formula (1):

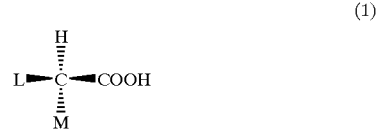

(1)

wherein L and M have the same meanings as defined in general formula (2), to contact with a microbiological material having an ability to convert the carboxylic acid isomer A into the carboxylic acid isomer B; and
separating the carboxylic acid isomer B,
wherein said microbiological material comprises a microorganism selected from the group consisting of *Nocardia diaphanozonaria, Saccharopolyspora hirsuta* and mutants thereof which are capable of converting the carboxylic acid isomer A into the carboxylic acid isomer B.

2. The process according to claim 1, wherein L in the carboxylic acid isomer A(1) is a $C_6$ to $C_{14}$ aryl group which 3. The process according to claim 1, wherein M in the carboxylic acid isomer A(1) is a methyl group.

4. The process according to claim 1 wherein the microbiological material is a cultured broth of microbial cells, microbial cells or materials obtainable by treating a microorganism of *Nocardia diaphanozonaria* JCM 3208 or a mutant thereof which is capable of converting the carboxylic acid isomer A into the carboxylic acid isomer B.

5. The process according to claim 1 wherein the microbiological material is a cultured broth of microbial cells, microbial cells or materials obtainable by treating a microorganism of *Saccharopolyspora hirsuta* subsp kobensis JCM 9109 or a mutant thereof which is capable of converting the carboxylic acid isomer A into the carboxylic acid isomer B.

6. A process for improving the optical purity of a composition containing a carboxylic acid represented by the general formula (3):

$$L\text{---}CH(M)\text{---}COOH \qquad (3)$$

wherein L is a $C_6$ to $C_{14}$ aryl group which may optionally be substituted, a $C_4$ to $C_{12}$ heteroaryl group which may optionally be substituted, a $C_6$ to $C_{14}$ aryloxyl group which may optionally be substituted or a $C_4$ to $C_{12}$ heteroaryloxy group which may optionally be substituted, and M is a $C_1$ to $C_3$ alkyl group which comprises contacting said composition with a microbiological material having an ability to convert the carboxylic acid isomer A represented by the general

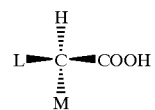

(1)

wherein L and M have the same meanings as defined in general formula (3) into the carboxylic acid isomer B represented by the general formula (2):

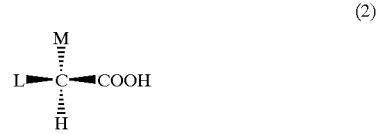

(2)

wherein L and M have the same meanings as defined in general formula (3),
wherein said microbiological material comprises a microorganism selected from the group consisting of *Nocardia diaphanozonaria, Saccharopolyspora hirsuta* and mutants thereof which are capable of converting the carboxylic acid isomer A into the carboxylic acid isomer B.

7. The process according to claim 6, wherein the composition of formula (3) is a mixture containing the carboxylic acid isomer A of formula (1) and the isomer B of formula (2).

8. The process according to claim 7, wherein the mixture is a racemic mixture.

* * * * *